US007349103B1

(12) United States Patent
Balooch et al.

(10) Patent No.: US 7,349,103 B1
(45) Date of Patent: Mar. 25, 2008

(54) SYSTEM AND METHOD FOR HIGH INTENSITY SMALL SPOT OPTICAL METROLOGY

(75) Inventors: Mehdi Balooch, Berkeley, CA (US); Marc Aho, Mountain View, CA (US); Homan Amin, San Jose, CA (US); Abdul Rahim Forouhi, Cupertino, CA (US); Phillip Walsh, San Jose, CA (US); Guoguang Li, Fremont, CA (US)

(73) Assignee: n&k Technology, Inc., Santa Clara, CA (US)

( * ) Notice: Subject to any disclaimer, the term of this patent is extended or adjusted under 35 U.S.C. 154(b) by 287 days.

(21) Appl. No.: 11/264,733

(22) Filed: Oct. 31, 2005

(51) Int. Cl.
*G01B 11/24* (2006.01)
(52) U.S. Cl. .................................................. 356/601
(58) Field of Classification Search ........ 356/630–632, 356/237.1–237.6, 124, 218, 300, 317, 319, 356/498, 613, 625; 250/372; 359/797; 430/8
See application file for complete search history.

(56) References Cited

U.S. PATENT DOCUMENTS

| 1,961,964 A | | 6/1934 | Dodge | |
|---|---|---|---|---|
| 2,064,252 A | | 12/1936 | Fortney | |
| 3,937,576 A | * | 2/1976 | Schmider | 356/300 |
| 4,611,143 A | | 9/1986 | Shimazu | 313/111 |
| 5,517,312 A | | 5/1996 | Finarov | 356/386 |
| 5,686,993 A | | 11/1997 | Kokubo | 356/381 |
| 5,910,842 A | | 6/1999 | Piwonka-Corle | 356/369 |
| 5,917,594 A | | 6/1999 | Norton | 356/327 |

(Continued)

FOREIGN PATENT DOCUMENTS

JP 2005017140 A * 1/2005

OTHER PUBLICATIONS

Zaidi, Shoaib et al., "FTIR-Based Non-Destructive Method for Metrology of Depths in Poly Silicon Filled Trenches," Metrology, Inspection and Process Control for Microlithography XVII, Proceedings of SPIE vol. 5038, 2003.

(Continued)

*Primary Examiner*—Tarifur Chowdhury
*Assistant Examiner*—Isiaka O Akanbi
(74) *Attorney, Agent, or Firm*—Lumen Patent Firm, Inc.

(57) ABSTRACT

An apparatus and method for examining features of a sample with a broadband beam of light obtained from a long-wavelength source that may include two distinct emitters that emit a long-wavelength radiation and a short-wavelength source that emits a short-wavelength radiation. A passage is positioned between the sources and a reflective beam combining optics is provided for shaping the long-wavelength radiation to enter the short-wavelength source via the passage and also for shaping the short-wavelength radiation that exits through the passage and propagates toward the long-wavelength source. The reflective beam combining optics shape the short-wavelength radiation such that it re-enters the short-wavelength source via the passage and is combined with the long-wavelength radiation into the broadband beam that exits the short-wavelength source. A beam steering optics projects the broadband beam to a spot on the sample, and a scattered broadband radiation from the spot is intercepted and shaped to a broadband signal beam, which is passed through a sampling pinhole that passes a test portion of it on to a detector for optical examination; the test portion that is passed can correspond to a center portion of the spot.

30 Claims, 12 Drawing Sheets

U.S. PATENT DOCUMENTS

| | | | |
|---|---|---|---|
| 5,972,469 A | 10/1999 | Curtis | 428/131 |
| 6,268,917 B1 | 7/2001 | Johs | 356/369 |
| 6,323,946 B1 | 11/2001 | Norton | 356/327 |
| 6,563,571 B1* | 5/2003 | Nuzzio | 356/51 |
| 6,583,877 B2 | 6/2003 | Norton | 356/369 |
| 6,690,111 B1 | 2/2004 | Davenport | 313/613 |
| 6,734,967 B1 | 5/2004 | Piwonka-Corle | 356/369 |
| 6,862,090 B2 | 3/2005 | Chen | 356/300 |
| 2002/0024669 A1 | 2/2002 | Danner | 356/369 |
| 2002/0030813 A1 | 3/2002 | Norton | 356/327 |
| 2002/0171830 A1 | 11/2002 | Norton | 356/369 |
| 2003/0020912 A1 | 1/2003 | Norton et al. | 356/369 |
| 2003/0133102 A1 | 7/2003 | Opsal | 356/237.1 |
| 2004/0008349 A1 | 1/2004 | Norton | 356/369 |
| 2004/0100632 A1 | 5/2004 | Piwonka-Corle et al. | 356/364 |
| 2005/0105090 A1 | 5/2005 | Piwonka-Corle et al. | 356/369 |

OTHER PUBLICATIONS

Guittet, P.-Y., et al., "Infrared Spectroscopic Ellipsometry in Semiconductor Manufacturing," Metrology, Inspection and Process Control for Microlithography XVII, Proceedings of SPIE vol. 5375, 2004.

* cited by examiner

SYSTEM AND METHOD FOR HIGH INTENSITY SMALL SPOT OPTICAL METROLOGY

FIELD OF THE INVENTION

This invention relates generally to systems and methods that employ a compound broadband light source for performing optical measurements with broadband beams that exhibit a high intensity and small spot size.

BACKGROUND ART

There are a number of applications and devices, which require for operation light that spans a broad wavelength spectrum. Since individual sources of light are only efficient in spanning portions of the broad wavelength spectrum needed, compound or composite light sources have been designed for these applications and devices. In particular, when the broad wavelength spectrum includes the ultraviolet (UV) and visible wavelengths two sources are usually combined into a broadband source covering this spectrum. This situation is encountered, for example, in scatterometry applications and devices where broad band light obtained from the compound source is used for determining optical properties of various materials as well as film thicknesses, geometric profiles of gratings and contact holes as well as many other non-destructive small-scale measurements.

The combining of individual light sources to produce a single broadband output beam that satisfies the constraints imposed by the measurement method is a complex task. To accomplish this task, light from a first source and light from a second source are combined with appropriate beam shaping and combining optics. Optics for efficiently capturing and shaping light from a single source are well-known. In fact, already in the electric lamp of U.S. Pat. No. 1,961,964 to Dodge a light shaping concave reflector is used for directing the light from a light source. Furthermore, U.S. Pat. No. 2,064,252 to Fortney teaches the use of incandescent lamp with a back reflector mirror to collimate the beam of light and increase illumination for use in automobile industry.

Of course, in building a compound light source, it is not sufficient to just efficiently capture light from a single source. It is also crucial that the light from the individual sources be efficiently combined. Here the prior art teaches to combine two sources covering the visible and the UV spectra, respectively. For example, in U.S. Pat. No. 4,611,143 Shimaza et al. teach the use of a deuterium lamp and a tungsten lamp in one sealed envelope to obtain a single broadband source. The tungsten lamp part of the system consists of a sealed envelope that forms a convex lens that focuses the visible light into the ARC aperture of the UV light generator. A concave mirror arranged behind the tungsten lamp reflects light emitted behind the filament back to the tungsten filament so as to maximize the quantity of light in the form of a beam at the location of the convex lens.

A more specific illumination system especially designed for measuring film thickness in described in U.S. Pat. No. 5,686,993 to Kokubo et al. Here, the inventors have combined halogen and deuterium lamps to form a broadband source that uses an off axis ellipsoidal reflector and half mirror to direct the combined broadband beam at the surface of the sample. The system includes a glass rod that corrects the wavelength dependence of the deuterium and halogen lamps, even when an eclipse in reflected light due to inclination of the sample decreases the energy of the reflected light. As a result, the spectral distribution of the reflected light entering a spectrometer unit remains almost unchanged.

Operating on broadband light beams places stringent constraints on the types of optics used. In particular, refractive optics such as lenses, tend to perform poorly and all reflective optics may be preferred for such applications. Although not a dual-source, teachings on how to use reflective optics in broadband spectroscopic ellipsometry are found in U.S. Pat. No. 5,910,842 to Piwonka-Corle et al. Here an Xe arc lamp is used as the source and two off-axis parabolic mirrors are employed to focus the light into a fiber optics. Further specific improvements to guiding light from sources such as deuterium lamps are found in U.S. Pat. No. 5,972,469 to Curtis, who teaches the use of an improved baffle to direct the light discharged from a deuterium lamp to increase light intensity and directionality and obtain reduction in ring formation.

More recent work has also focused on combining more than two sources and achieving a flattened intensity distribution in broadband beams for optical measurements in ellipsometers, spectrophotometers and polarimeters. For example, in U.S. Pat. No. 6,268,917 Johs teaches combining Xe, deuterium and quartz halogen lamps to obtain near flat broadband beam for material system investigation. Still other approaches to combining two sources for coaxial illumination for optical metrology are found, e.g., in U.S. Pat. No. 6,862,090 to Chen et al. and in U.S. Patent Application 2003/0020912 to Norton et al.

Unfortunately, none of the prior art solutions provides for a broadband light source that efficiently combines sources, provides a reasonably flat spectrum and achieves suitably high intensity at a correspondingly small spot size for examination of samples with small features. In fact, although today a 50×50 $\mu m^2$ test pad is used as a standard size in semiconductor manufacturing devices, as the packing density increases and features are shrinking there is increased demand for smaller test pads. Conventionally, the spot size reduction is accomplished by application of refractive lenses. However, in a broadband system these lenses add complication such as aberration and require frequent alignments. Moreover, addition of refractive lenses frequently contributes to significant reduction in light intensity.

OBJECTS AND ADVANTAGES

In view of the above prior art limitations, it is an object of the invention to provide an apparatus and method for examining small features or structures of a sample with a broadband beam that is high intensity and is simultaneously capable of focusing down to a small spot size on the sample. In particular, the object of the invention is to provide such apparatus and method for optical metrology and optical scatterometry in particular.

It is another object to provide an apparatus that can be used in various optical metrology methods that examine material properties, critical dimensions (CDs) and make profile determination of patterned sample surfaces using only reflective optics.

These and other objects and advantages of the invention will become apparent from the ensuing description.

SUMMARY OF THE INVENTION

The objects and advantages of the invention are addressed by an apparatus for examining features of a sample with a broadband beam of light. The apparatus has a long-wavelength source for emitting a long-wavelength radiation and a short-wavelength source for emitting a short-wavelength radiation with a passage positioned between these two sources. A reflective beam combining optics is provided for shaping the long-wavelength radiation to enter the short-wavelength source via the passage and also for shaping the short-wavelength radiation that exits through the passage and propagates to the long-wavelength source. The reflective beam combining optics shapes the short-wavelength radiation such that it re-enters the short-wavelength source via the passage and in the process is combined with the long-wavelength radiation into the broadband beam that exits the short-wavelength source and propagates to the sample. The apparatus is further equipped with a beam steering optics for projecting the broadband beam to a spot on the sample. A scattered broadband radiation originating from the spot is intercepted by a beam intercepting optics and shaped to produce a broadband signal beam, which is passed through a sampling pinhole that passes a test portion of the signal beam on to a detector for performing optical examinations. More specifically, the test portion that is passed on for examination corresponds to a center portion of the spot.

In a preferred embodiment of the invention the long-wavelength source has two distinct emitters. The first is a visible wavelength emitter for emitting a visible radiation and the second is an infrared wavelength emitter for emitting an infrared radiation. Appropriate beam combining mechanism is provided for combining the visible radiation and the infrared radiation into a beam of long-wavelength radiation. Alternatively, the long-wavelength source uses the visible and infrared radiation one at a time. This can be accomplished in many ways. For example, a mobile stage can be provided for moving the emitters from between the reflective beam combining optics and the passage.

The reflective beam combining optics are preferably embodied by a concave reflector, such as a spherical mirror or an ellipsoidal mirror. To ensure that the reflector operates well over the entire broadband spectrum, it is advantageous to provide it with a broadband reflective coating on the reflective surface. In the event that the reflector is spherical, a refractive element can be positioned between the long-wavelength source and the passage for further shaping the long-wavelength radiation and short-wavelength radiation to ensure that it properly enters the short-wavelength source via the passage. In some specific embodiments, the long-wavelength source and the refractive element are mounted together on a second mobile stage such that they can be inserted and removed from between the concave reflector and the passage. This may be done, for example, to perform a measurement of the sample with the short-wavelength radiation only.

Various sources can be used to provide the short- and long-wavelength radiation. For example, the short-wavelength source can be DUV deuterium lamp and the long-wavelength source is a halogen lamp or a discharge lamp. Preferably, the short-wavelength source has a wide-band transparent casing, e.g., bulb casing, which permits the entire broadband spectrum to pass through without appreciable absorptive losses. Materials such as magnesium fluoride ($MgF_2$) and synthetic silica can be used for this purpose.

In a preferred embodiment, the long-wavelength source and the short-wavelength source are fitted in a common housing and are both provided with fittings for attachment to the housing. In this manner a precise relationship, both in terms of separation and alignment of the two sources, can be more easily enforced in the apparatus.

In another embodiment of the invention the apparatus has a first configurable optics for shaping the long-wavelength radiation to enter the short-wavelength source via the passage. A second configurable optics are provided for shaping the short-wavelength radiation exiting through the passage to re-enter the short wavelength source through the passage. In this embodiment the first configurable optics preferably include an ellipsoidal mirror and a removable plane mirror. The second configurable optics can include a spherical mirror.

Embodiments employing first and second configurable optics are particularly useful when the configurable optics are movable. By virtue of being movable, the optics can be configured or arranged such that only the short- or the long-wavelength radiation is projected to the spot on the sample. In other words, measurements with only a portion of the broadband radiation can be performed in these embodiments. In any of these configurations, the long-wavelength source can include a visible wavelength emitter and an infrared wavelength emitter.

The objects and advantages of the invention are further addressed by a method for examining features of a sample with short- and long-wavelength radiation. In accordance with the method, the long- and short-wavelength radiation can be projected at the spot at the same time or at different times. Furthermore, for testing purposes, it is useful to limit the cross-section of the radiation, e.g., by providing another optical element such as a pinhole or by passing a knife edge over the cross-section of the light beam.

A detailed description of the preferred embodiments of the invention is presented below in reference to the appended drawing figures.

BRIEF DESCRIPTION OF THE DRAWING FIGURES

Figure 4A:
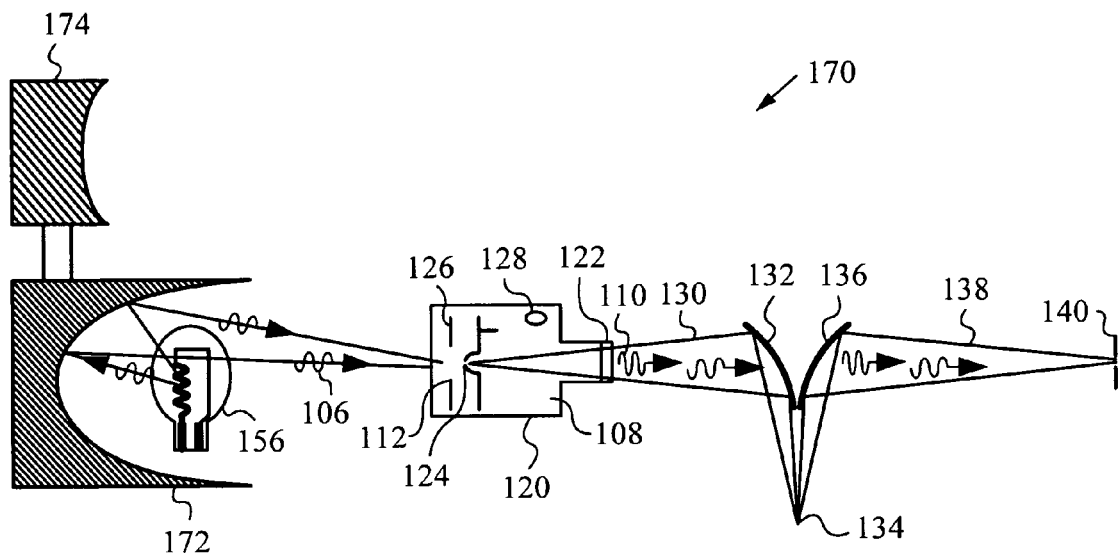

FIGS. 4A&B are side views of another apparatus with configurable optics in two settings.

Figure 5:
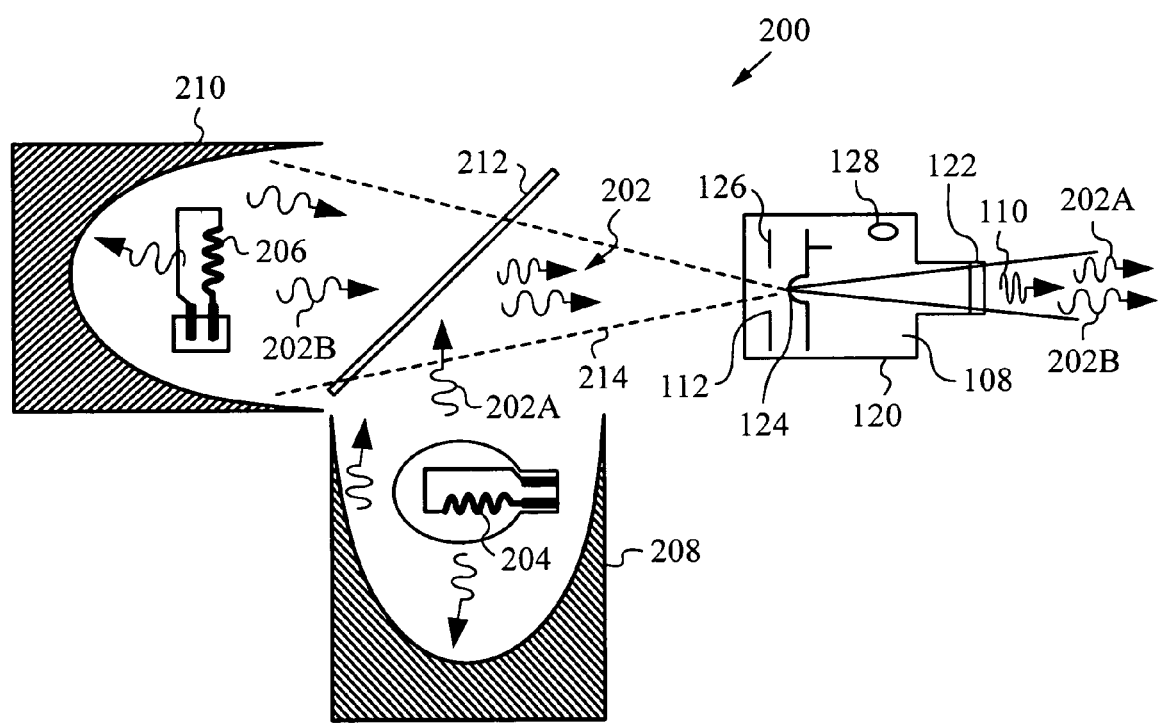

FIG. 5 is a side view of an apparatus employing one short-wavelength source and two emitters for generating long-wavelength radiation.

Figure 6:
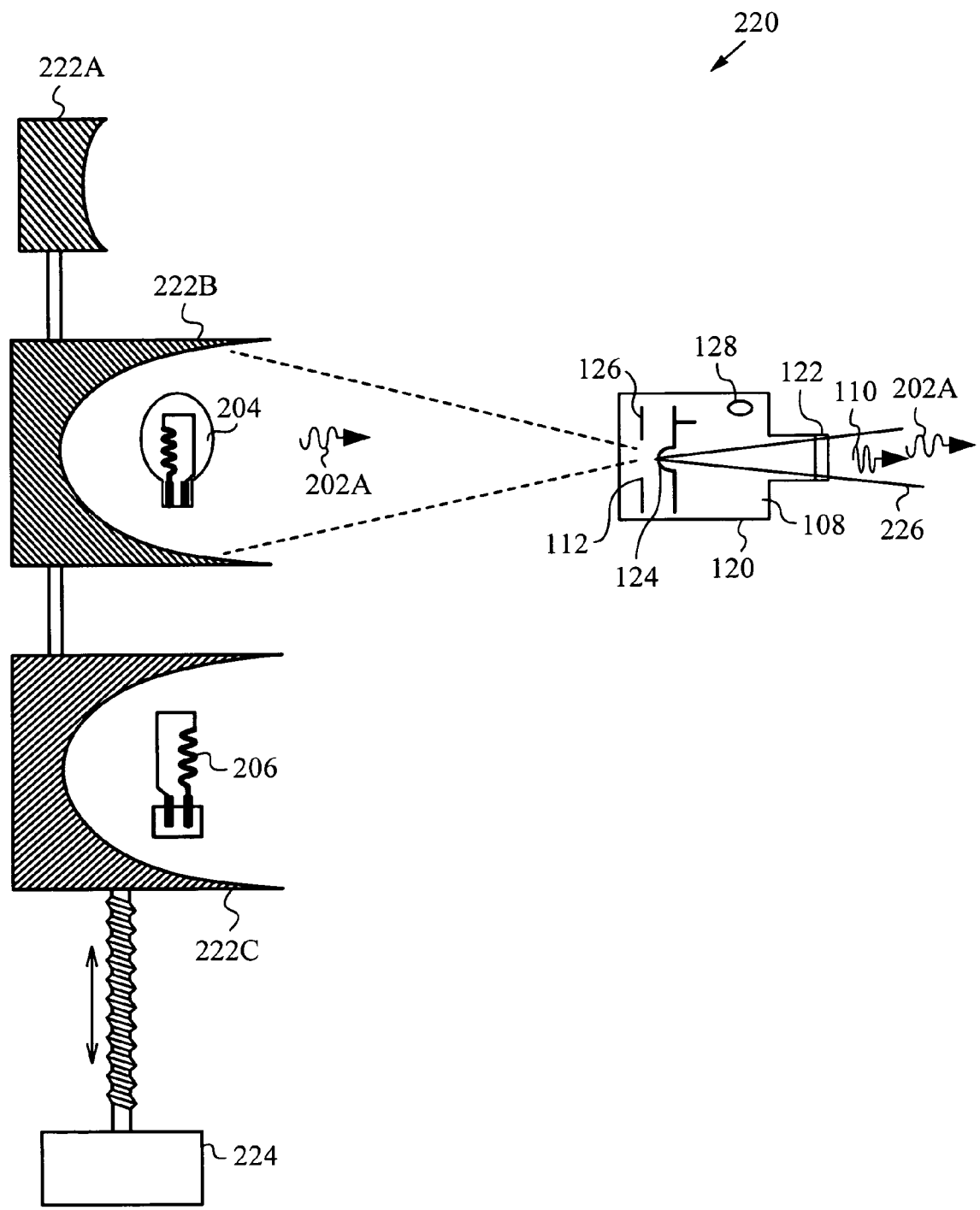

FIG. 6 is a side view of an apparatus employing configurable optics with a short-wavelength source an two emitters for generating long-wavelength radiation.

Figure 7A:
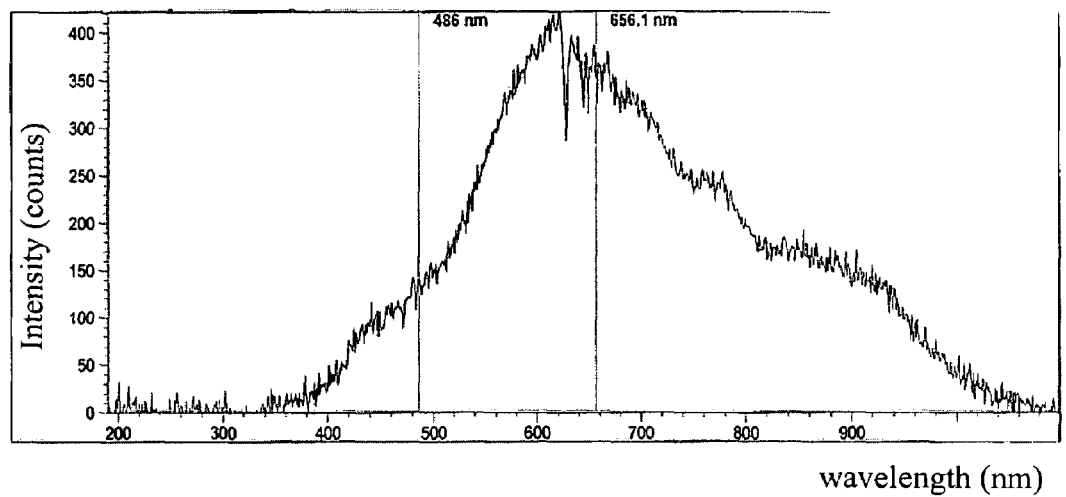

FIGS. 7A&B are graphs illustrating intensity characteristics as a function of wavelength for a tungsten (W) and halogen long-wavelength sources.

Figure 8A:
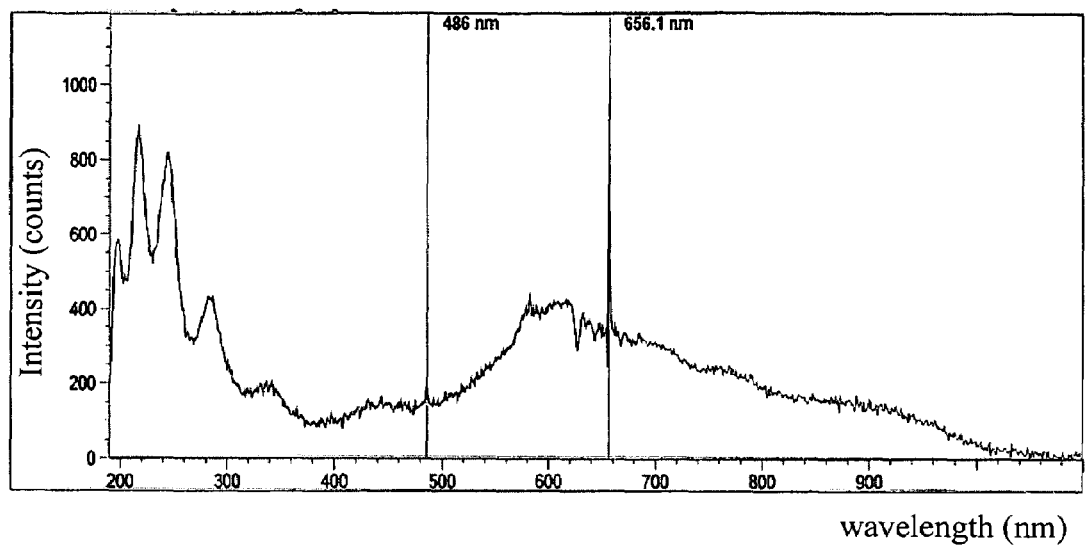

FIGS. 8A&B are graphs illustrating intensity characteristics for two source combinations over the entire broadband spectral range.

Figure 9:
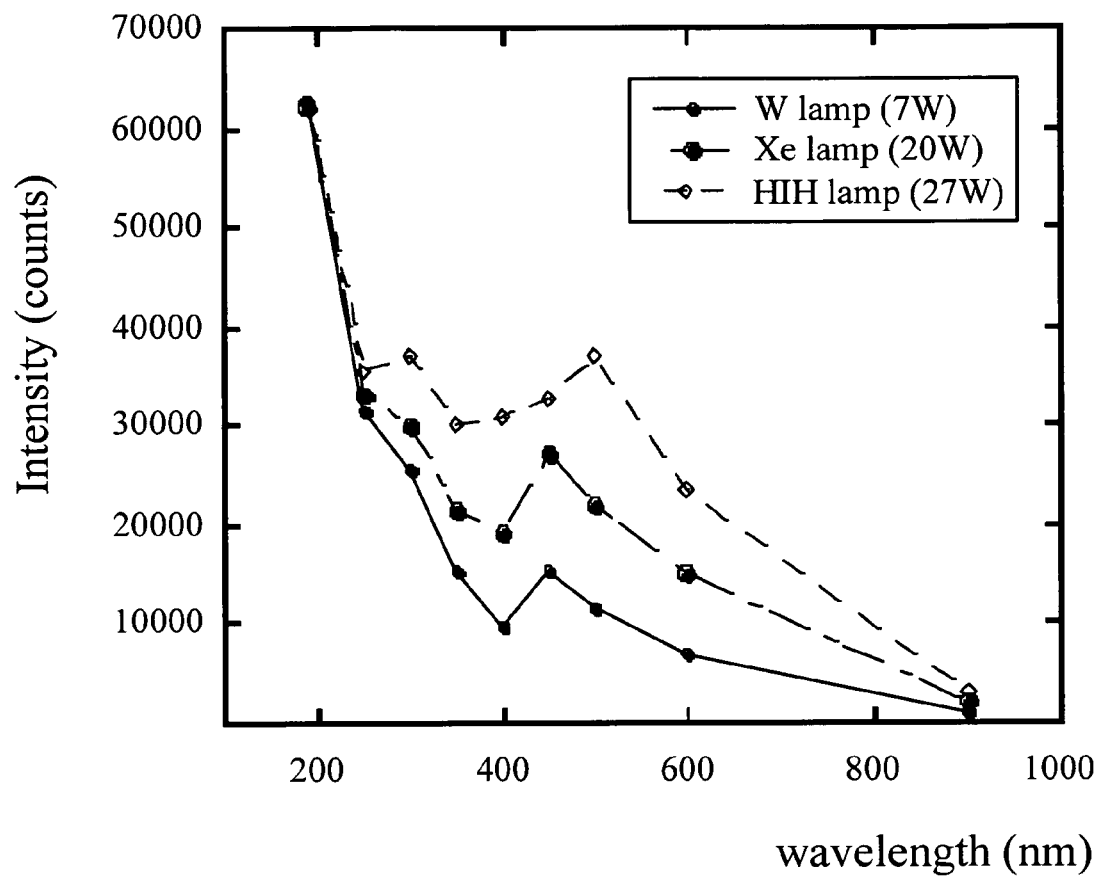

FIG. 9 is a graph comparing several long-wavelength sources that can be used in the apparatus of invention.

Figure 10:
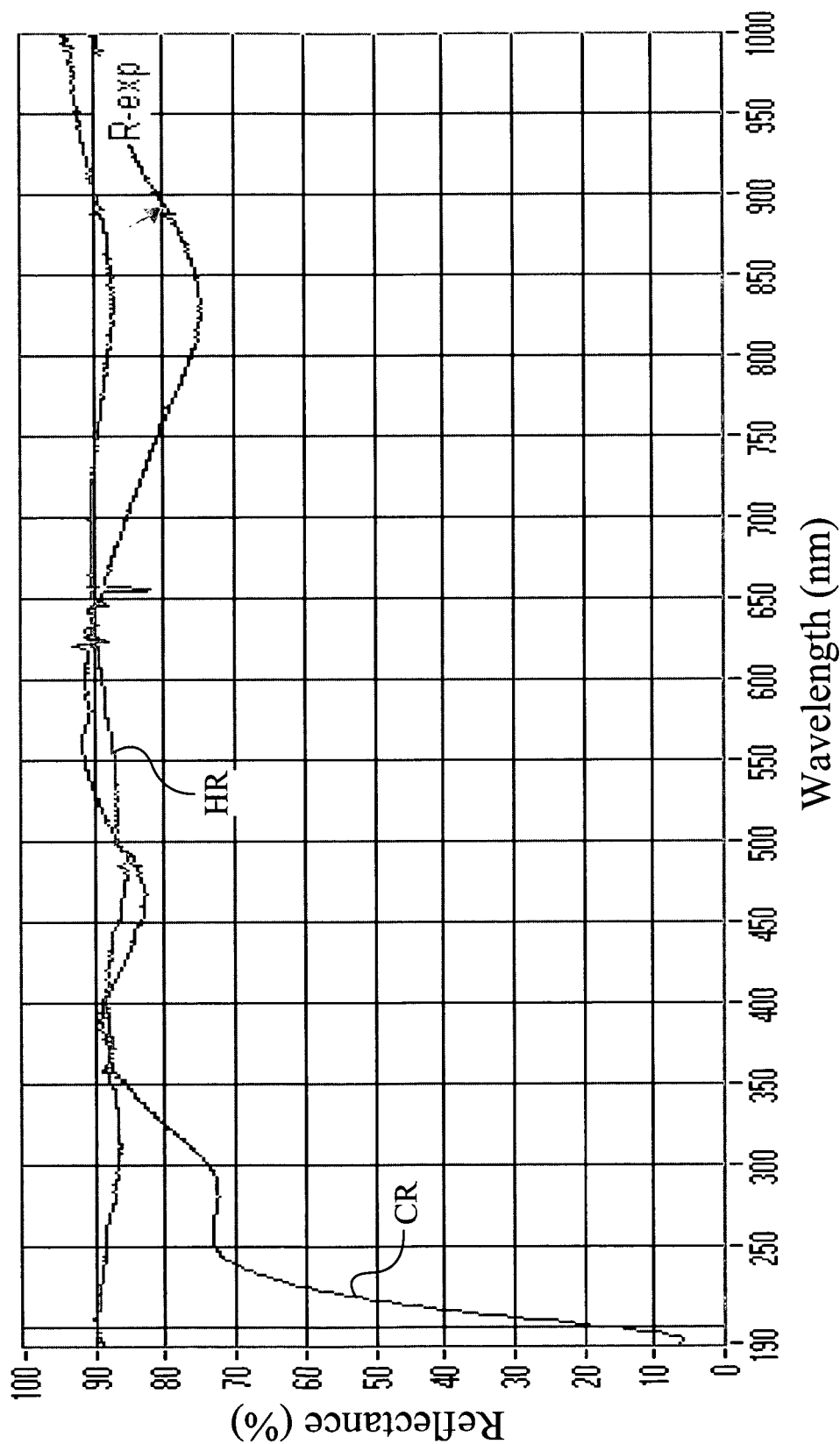

FIG. 10 is a graph comparing the performance of beam combining reflective optics with conventional reflective films and highly reflective silver coated-films.

Figure 11:
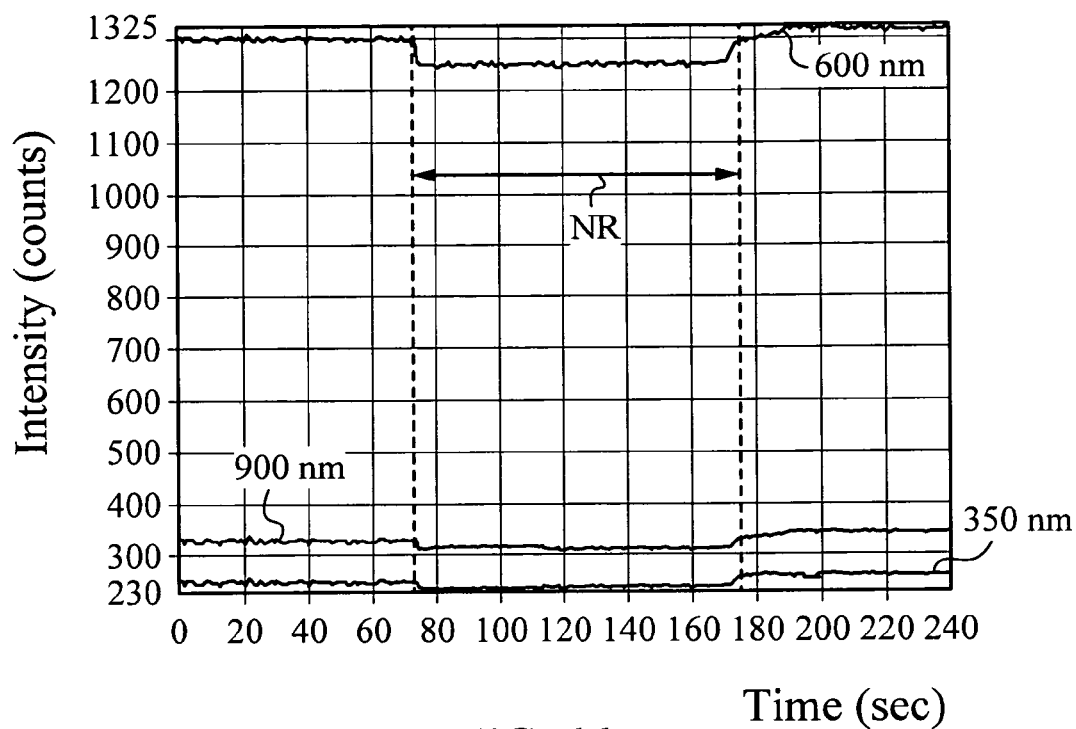

FIG. 11 illustrates the effects of reflective beam combiner with coating on three wavelengths when using halogen and deuterium lamps.

Figure 12:
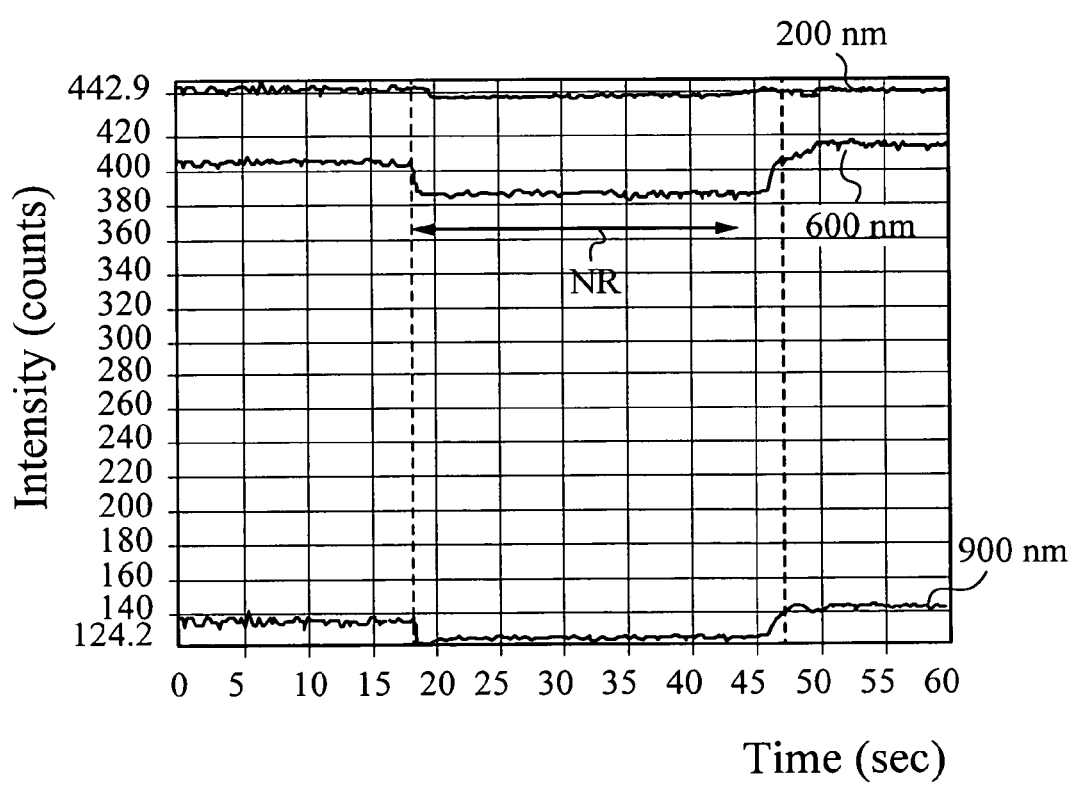

FIG. 12 illustrates the effects of reflective beam combiner with coating on three wavelengths when using tungsten and deuterium lamps.

Figure 13:
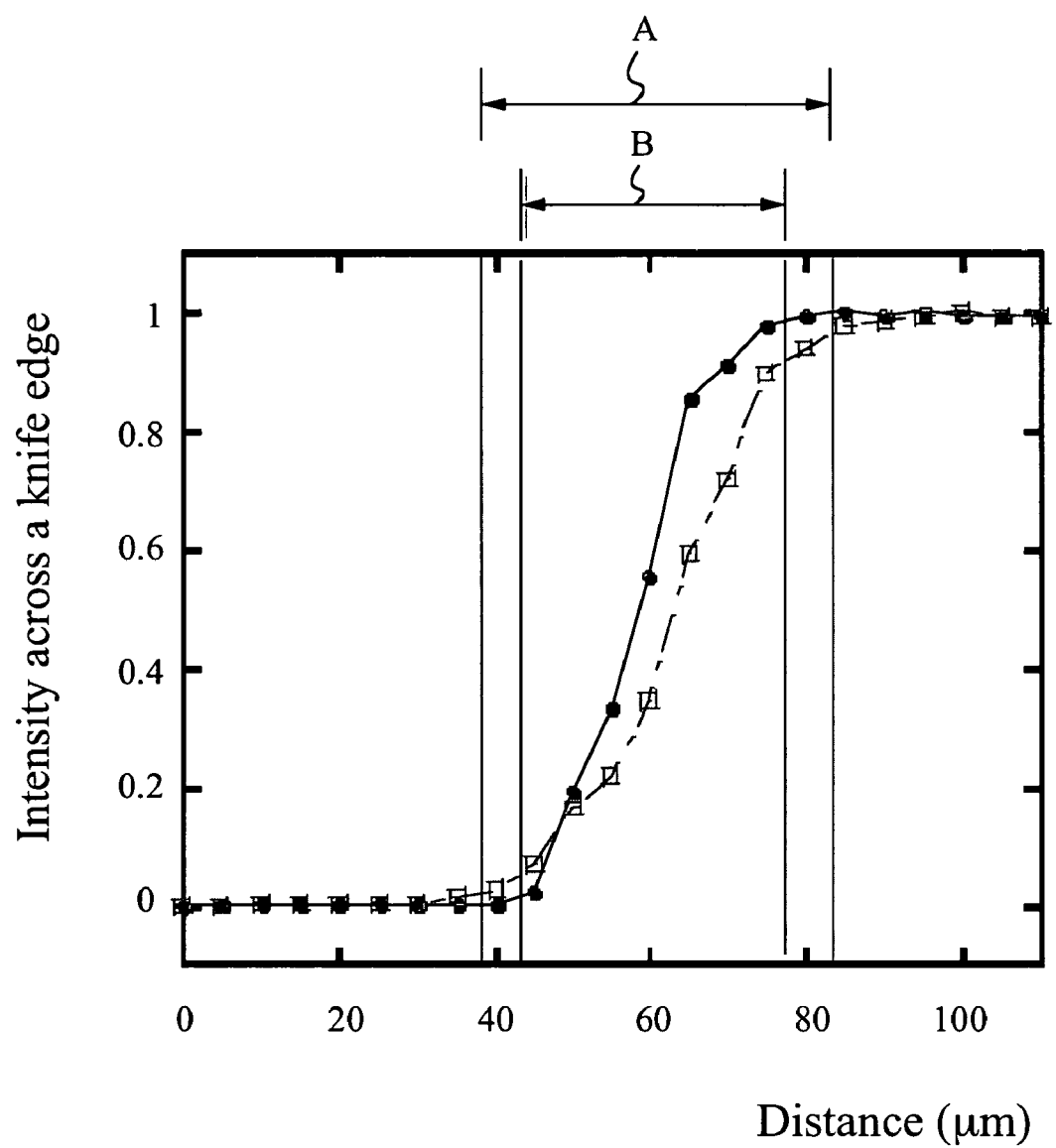

FIG. 13 is a graph showing the sampling performed by the sampling pinhole at 20 μm and 40 μm.

Figure 14:
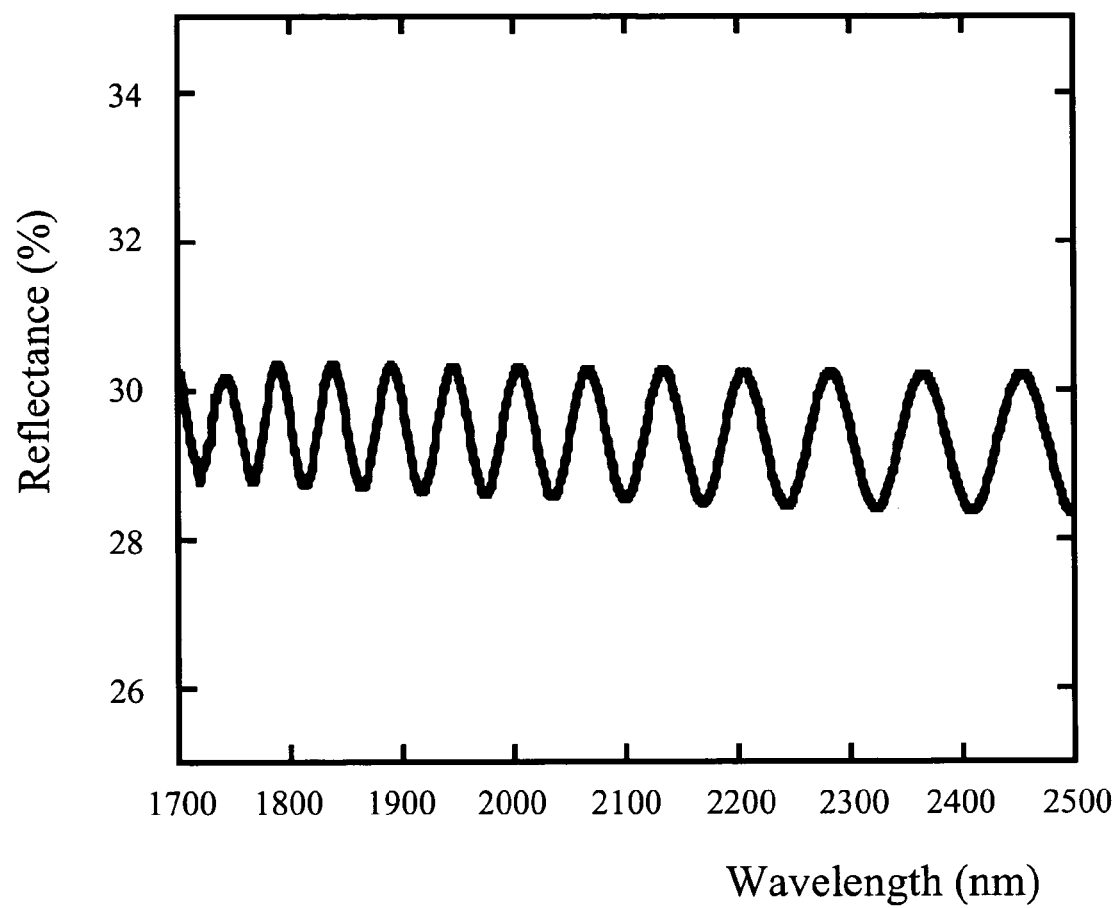

FIG. 14 is a graph showing a simulated reflectance IR spectrum obtained with an apparatus of invention at an angle incidence of 0.4 degrees for the broadband beam onto a sample having a three-dimensional structure etched in silicon.

DETAILED DESCRIPTION

Figure 1:
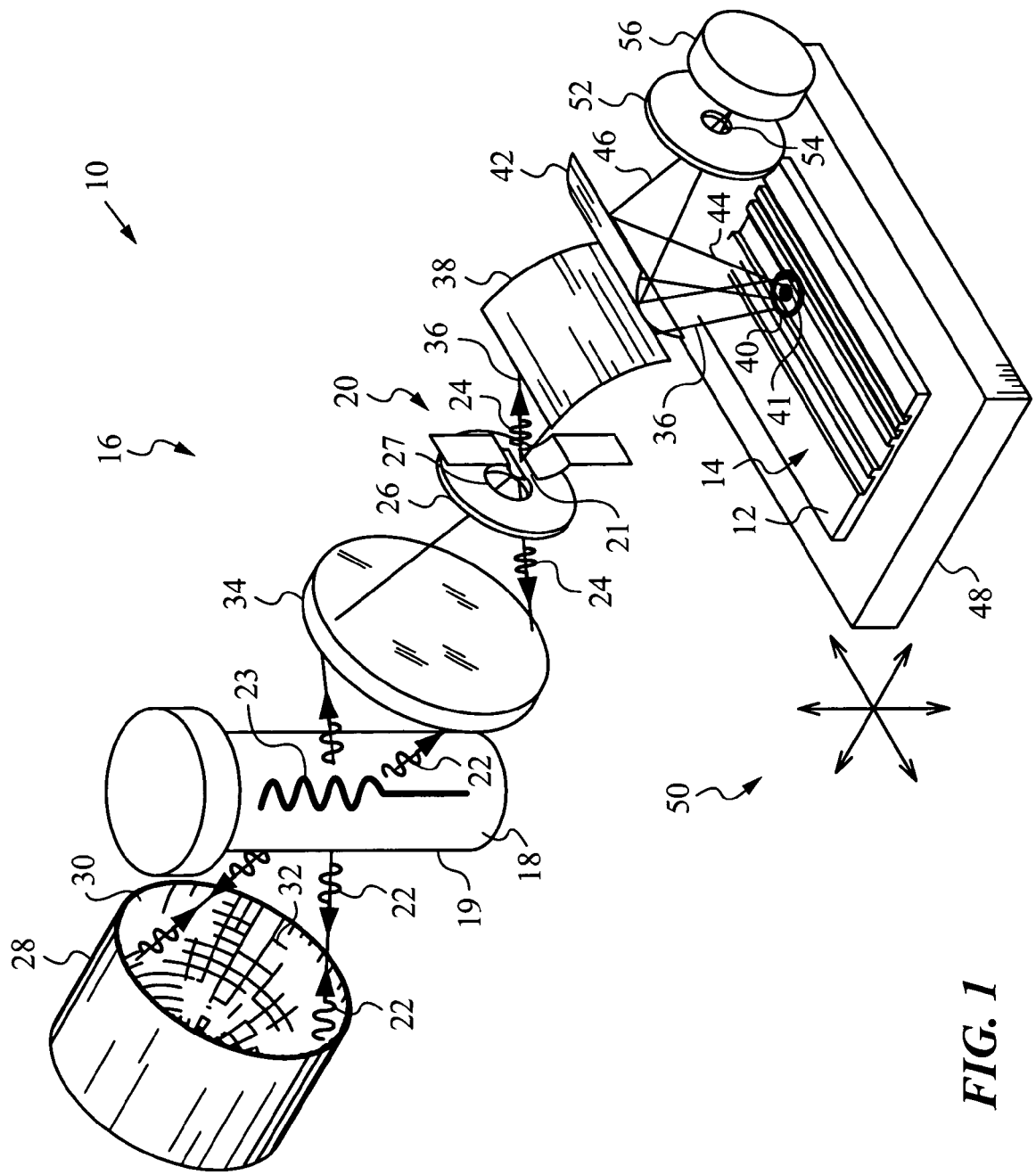
FIG. 1 is a three-dimensional diagram illustrating the basic components and principles of the invention.

The present invention and its principles will be best understood by first referring to an apparatus 10 for examining features 14 of a sample 12, as shown in FIG. 1. Apparatus 10 has a compound source of light 16 that includes a long-wavelength source 18 for emitting a long-wavelength radiation 22 and a short-wavelength source 20 for emitting a short-wavelength radiation 24.

Long-wavelength source 18 is a lamp, e.g., a halogen lamp or a discharge lamp for emitting long-wavelength radiation 22 from a filament 23. Of course, other sources capable of emitting a long-wavelength radiation 22 spanning the appropriate bandwidth, i.e., visible to infrared, e.g., from about 250 nm to 900 nm or even up to 3,000 nm and above may also be used. The long-wavelength sources can themselves be compound, i.e., they may employ two or more separate emitters of different spectral portions of long-wavelength radiation 22. In any event, a casing 19 of lamp 18 is made of a wide-band transparent material such as quartz, $MgF_2$ or synthetic silica to ensure high transmissivity to long-wavelength radiation 22 as well as short-wavelength radiation 24. Further, it is important that source 18 emit radiation 22 at a high intensity in the visible portion of the spectrum.

Preferably, short-wavelength source 20 is a deep ultra-violet (DUV) deuterium lamp relying on gas discharge (not shown) for emitting short-wavelength radiation 24 covering a bandwidth from about 250 nm to less than 190 nm. Of course, other sources capable of emitting radiation 24 in this bandwidth can also be used. In the present embodiment, DUV deuterium lamp 20 has a small (0.5 mm or even narrower) aperture or slit 21 (also referred to as an ARC aperture), separating a cathode (not shown) and an anode 26. This arrangement causes charge to be accelerated through aperture 21 on its path to anode 26 resulting in a "point-source-like" emission of UV radiation 24 at aperture 21. Thus, aperture 21 acts as a point source of short-wavelength radiation 24.

The envelope or casing (see FIG. 2) of UV source 20 is wide-band as is made of materials that are transparent to long- and short-wavelength radiation 22, 24. Aperture 21 controls the passage of radiation 22, 24 and blocks off the unwanted or unstable cathode glow radiation. It also assists in preventing sputtered material from reaching the exit window of source 20 (see FIG. 2) that is made of highly transparent, from DUV to visible, material such as quartz, $MgF_2$ or synthetic silica.

A passage 27 is located between sources 18 and 20. In the preferred embodiment, passage 27 is a wide aperture or entrance hole provided directly in anode 26. Passage 27 permits short-wavelength radiation 24 and long-wavelength radiation 22 to pass through it unobstructed in either direction. A reflective beam combining optics 28 terminates apparatus 10 and it is positioned to intercept any radiation propagating away from sources 18, 20 and sample 12. In the present embodiment, optics 28 is a concave reflector and more precisely still, a spherical mirror. Mirror 28 is positioned to reflect and shape, or more precisely focus long-wavelength radiation 22 back into source 18. Similarly, mirror 28 also reflects and focuses short-wavelength radiation 24 back into source 18. The focusing is such that long-wavelength radiation 22 passes through passage 27 and combines with short-wavelength radiation 24 coming to a focus at aperture 21. Therefore, aperture 21 acts not only as a point source of short-wavelength radiation 24 but also like a point source of long-wavelength radiation 22. As a result, aperture 21 is effectively a point source of a broadband beam 36 that combines long- and short-wavelength radiation 22, 24.

A reflective surface 30 of mirror 28 is coated with a broadband reflective coating 32 to ensure that mirror 28 operates well over the entire bandwidth spanned by long- and short-wavelength radiation 22, 24, namely from below 190 nm up to about 3,000 nm. Among other materials, silver is a suitable reflective coating 32 that enhances reflectivity from ultra-violet all the way to infrared. Of course, other materials including multi-layer coatings can be used and it should be noted that such coatings and techniques for their application to surface 30 are familiar to those skilled in the art.

In addition to spherical mirror 28, a refractive element 34 is positioned between source 18 and passage 26. Refractive element 34 is a convex lens for further shaping long-wavelength and short-wavelength radiation 22, 24 to ensure that it properly enters short-wavelength source 20 via passage 27 in anode 26. In the case of short-wavelength radiation 24, mirror 28 and lens 34 are actually ensuring proper re-entry into source 20 of radiation 24 that exited source 20 through passage 27 to begin with; i.e., the portion of radiation 24 which would have been lost. In the case of long-wavelength radiation 22, mirror 28 captures a portion that would be lost and reflects it back through source 18 to lens 34 for focusing at aperture 21 through passage 27. The portion of long-wavelength radiation 22 that is already propagating toward source 20 also gets focused at aperture 21 by lens 34. Thus, in effect mirror 28 and lens 34 shape and combine long- and short-wavelength radiation 22, 24 and use aperture 21 as a point source of broadband beam 36 that ultimately exits source 20 and propagates towards sample 12.

Apparatus 10 has beam steering optics 38 for projecting broadband beam 36 to a spot 40 on sample 12. Although optics 38 can be refractive, they are preferably reflective. In the present embodiment, optics 38 are in the form of a reflector, and more precisely in the form of a toroidal mirror. Other curved mirrors, such as, e.g., parabolic can also be used.

A beam intercepting optics 42 are provided for intercepting a scattered broadband radiation 44 from spot 40. In other words, optics 42 are provided for collecting radiation 22, 24 scattered from spot 40 for optical metrology purposes. More specifically, optics 42 collects the scattered broadband radiation to produce a broadband signal beam 46 and sends it for examination. As in the case of optics 38, optics 42 can be refractive, but are preferably reflective. In the present embodiment, optics 42 are in the form of a curved reflector, and more precisely in the form of a toroidal mirror that cooperates with toroidal mirror 38 to enable irradiation of sample 12 and collection of scattered radiation 22, 24 at near-normal incidence. Note that mirror 42 can also have other curved shapes such as, e.g., parabolic.

For optical metrology purposes, sample 12 is positioned on a moving stage 48. As indicated by the arrows designating the coordinate system 50, stage 48 can be adjusted in any required direction to ensure that spot 40 can be directed at any of features 14 for measurement. Stage 48 can include any combination of linear and rotational drives for accomplishing this task.

A sampling pinhole 52 is positioned in the path of signal beam 46 for passing a test portion 54 thereof for examination. Test portion 54 corresponds to a center portion 41 of spot 40. Preferably, center portion 41 has a diameter of about 20 μm to about 40 μm when spot 40 has a diameter of 500 μm or more. In fact, sampling portion 54 can correspond to center portion 41 with a diameter as small as 5 μm for high accuracy optical metrology and scatterometry in particular.

Finally, apparatus 10 has a detector 56 positioned behind sampling pinhole 52 for examining sampling portion 54 corresponding to center portion 41 of spot 40. Detector 56 is a broadband detector and can be in the form of a photodiode array, CMOS linear array, CCD linear array or any other type of spectral detector.

Apparatus 10 is used for optical metrology, and preferably scatterometry in which the properties of sample 12, which can be a semiconductor wafer, and its features 14, such as gate circuitry, are examined in a non-destructive, optical manner. In particular, the optical methods of scatterometry are applied to determining material parameters as well as profiles of features 14 including their critical dimensions (CDs) and imperfections.

During operation, long- and short-wavelength radiation 22, 24 is combined and shaped into broadband beam 36 with the aid of mirror 28, lens 34 and ARC aperture 21. Because backward emitted radiation 22, 24, or, more precisely, portions of radiation 22, 24 propagating away from sources 18, 20 and sample 12, are saved by mirror 28 and lens 34, apparatus 10 is very light efficient. Thus, the intensity of broadband beam 36 arriving at the surface of sample 12 is higher across the entire spectrum when compared with prior art arrangements employing compound sources.

Figure 7B:
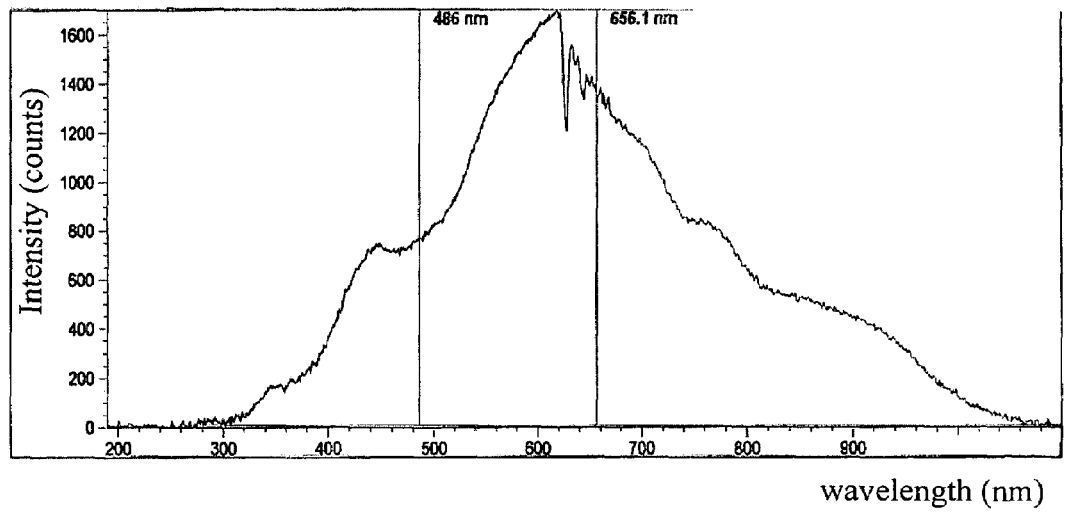

The graphs in FIGS. 7A and 7B compare the radiation intensity characteristics of a typical tungsten (W) lamp, which is used as source in prior art applications, with a halogen lamp that is employed in the preferred embodiment of the present invention. The graph in FIG. 7A shows absolute intensity counts for the wavelength shown, measured through a typical tungsten (W) and deuterium combined light source with the deuterium source turned off. In comparison, FIG. 7B shows the same system as in FIG. 7B, except in the place of the tungsten (W) source (bulb), is a halogen bulb. It is apparent that the halogen bulb provides a more intense light source. In fact, the intensity over the visible portion of the spectrum achieved with a halogen or high intensity discharge lamp is about 3 fold higher.

Figure 8B:
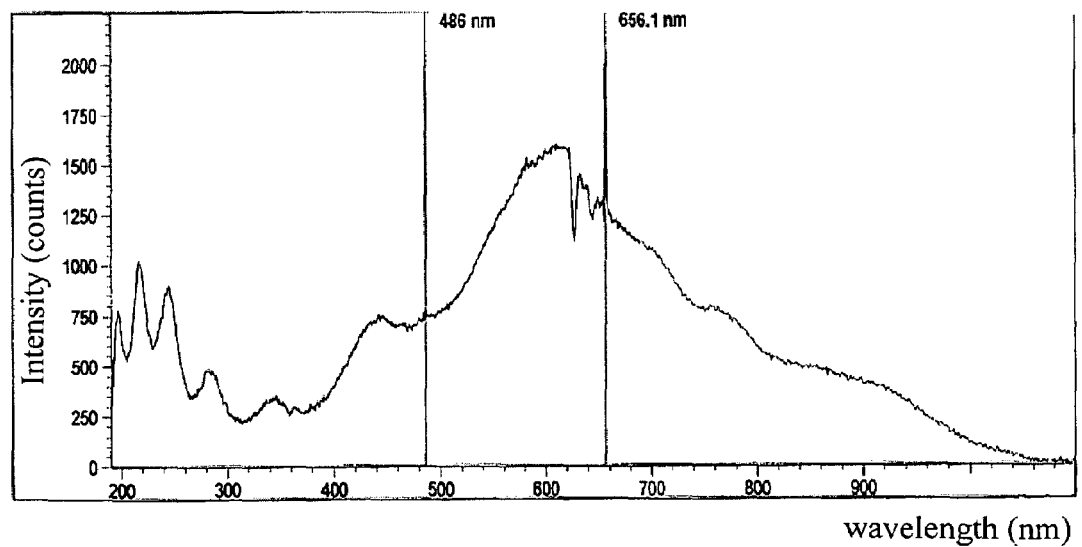

FIG. 8A shows the same system as in FIG. 7A except that the intensity is being measured with both the tungsten (W) and deuterium lamp on. FIG. 8B shows the same system as in FIG. 7B except that the intensity is being measured with both the halogen and deuterium lamps on. In comparison to the graphs in FIGS. 7A and 7B the spectral range is increased down to 190 nm when the deuterium bulb is turned on. It can also be seen that the halogen bulb increased the UV region slightly more in comparison to the tungsten bulb. The comparison of radiation intensity characteristics over the entire bandwidth for a compound source using a W lamp and a deuterium lamp (prior art) with the compound source of the invention employing a halogen lamp and a DUV deuterium lamp clearly shows intensity gains. Specifically, short-wavelength radiation 24 exhibits 5% higher intensity and long-wavelength radiation 22 exhibits intensity higher by at least a factor of three.

In addition to the increased radiation intensity over the entire bandwidth, apparatus 10 also produces a better-confined spot 40. That is because optics 38 are reflective and broadband beam 36 is well-focused as a result of ARC aperture 21 acting as a point source of beam 36. Thus, spot 40 is high quality and has a diameter of 500 μm or less since apparatus 10 is a one-to-one imaging system.

In addition to improvements in delivering broadband beam 36, sampling aperture 52 selects test portion 54 of signal beam 46 for examination to bring further advantages. These advantages are particularly apparent, when test portion 54 is set to correspond exactly to center portion 41 of spot 40 and is limited in its diameter to less than 30 μm while spot 40 has a diameter of 500 μm or more. In this configuration sampling aperture 52 selects the highest intensity portion of signal beam 46 for examination by detector 56. If the optical system is perfect and without any aberrations then sampling aperture 52 diameter can be increased to 50 μm when the system is designed for one-to-one imaging. However, in most cases one-to-one imaging systems have aberrations that require sampling aperture 54 to be smaller in diameters than the actual test portion measured.

Figure 2:
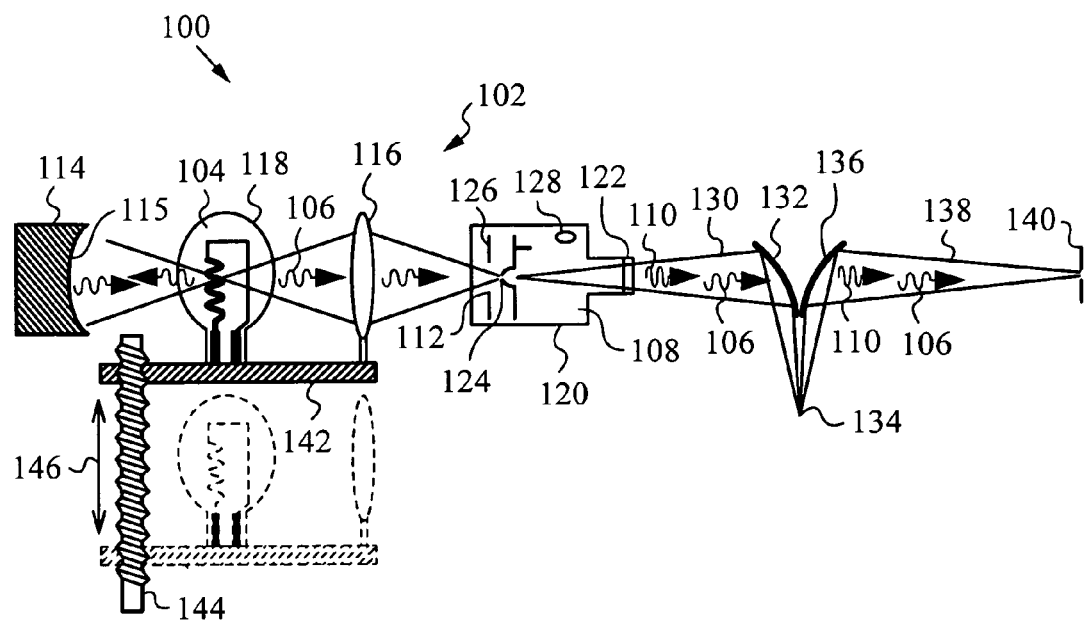
FIG. 2 is a side view of an apparatus according to the invention with a mobile stage carrying a long-wavelength source and a refractive element.

The apparatus of invention and its method can be practiced in various ways. For example, in an alternative embodiment, as shown in FIG. 2, an apparatus 100 for examining features of a sample (not shown) has a compound source 102 consisting of a long-wavelength source 104 in the form of a halogen lamp emitting a long-wavelength radiation 106, and a short-wavelength source 108 in the form of a DUV deuterium lamp emitting short-wavelength radiation 110. As in the previous embodiment, sources 104, 108 are separated by a passage 112. A spherical mirror 114 in conjunction with a convex lens 116 are used for shaping and combining short- and long-wavelength radiation 106, 110. A reflective surface 115 of mirror 114 is provided with a wideband coating, as in the previous embodiment.

In this embodiment, long-wavelength source 104 has a wide-band casing 118. Casing 118 is made of synthetic silica and is therefore highly transmissive to long- and short-wavelength radiation 106, 110. Alternatively, casing 118 is made of $MgF_2$ or quartz.

Short-wavelength source 108 is located in a casing 120 with an exit window 122. Window 122 is a wide-band window by virtue of also being made of synthetic silica. Alternatively, window 122 can be made of $MgF_2$ or quartz. Short-wavelength source 108 has a hole 124 or ARC aperture, separating an anode 126 and a cathode 128 and resulting in a "point-source-like" emission of short-wavelength radiation 110. ARC aperture 124 also acts as the focal point of long-wavelength radiation 106 to pass through and combine with short-wavelength radiation 110 to produce a broadband beam 130. Aperture 124 also controls the passage of radiation 106, 110 and blocks off the unwanted or unstable cathode glow radiation. It also assists in preventing sputtered material from reaching exit window 122 of source 120.

Spherical mirror 114, lens 116, passage 112 and ARC pinhole 124 act together to ensure that broadband beam 130 has a high intensity over its bandwidth and emerges from ARC pinhole 124 as if from a point source. After emerging from window 122, beam 130 encounters steering optics 132 that projects beam 130 to a spot 134 on a sample (not shown). Optics 132 are in the form of a toroidal or off-axis parabolic mirror.

Beam intercepting optics 136 are provided for collecting scattered broadband radiation returning from spot 134. Optics 136 also shape scattered radiation 106, 110 to form a broadband signal beam 138 and direct it to a detector (not shown) via a sampling pinhole 140 for optical metrology purposes. Optics 136 are in the form of a toroidal or off-axis parabolic mirror that cooperates with toroidal or off-axis parabolic mirror 132 to enable irradiation of the sample and collection of scattered radiation at near-normal incidence.

Long-wavelength source 104 and lens 116 are both mounted on a mobile stage 142. Stage 142 has a drive 144 for moving it in and out, as indicated by arrow 146. Drive 144 can be of any suitable type, including mechanical or electro-mechanical.

During operation, mobile stage 142 is moved in and out by drive 144 to insert and remove source 104 and lens 116 from between mirror 114 and passage 112. The ability to remove source 104 and lens 116 offers the user the ability to perform measurements with only short-wavelength radiation 110. When source 104 and lens 116 are inserted, the measurement is performed with both short- and long-wavelength radiation 106, 110. In an "in" configuration, the long-wavelength signal is maximized while in the "out" configuration the short-wavelength signal improves since no loss due to long-wavelength casing 118 exists.

Figure 3:
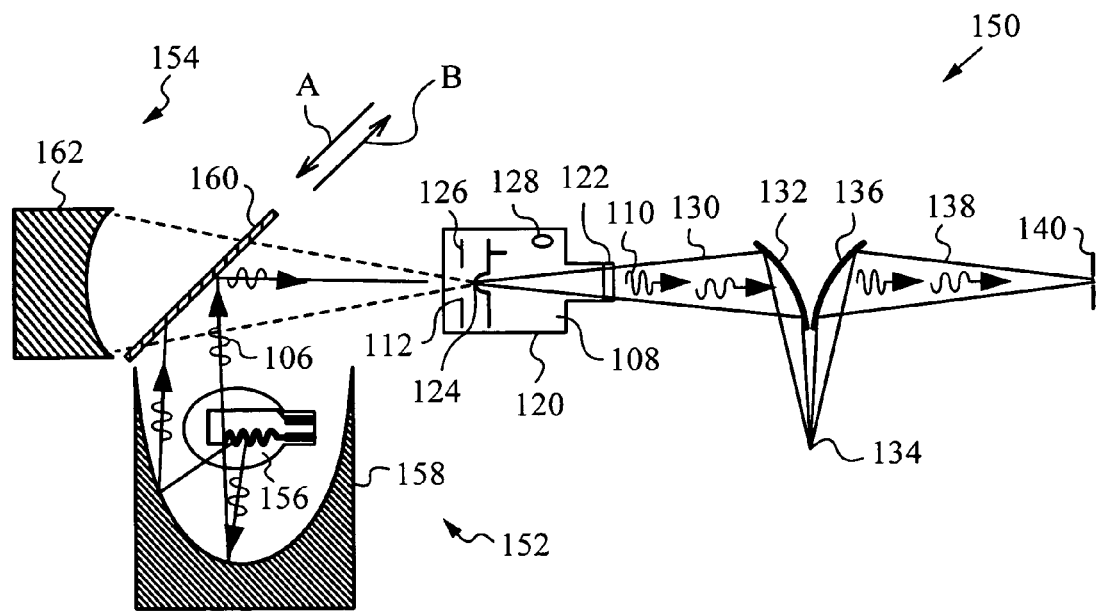
FIG. 3 is a side view of another apparatus of the invention with two configurable optics; the first in the form of an ellipsoidal mirror and a removable plane mirror.

In still another embodiment, as shown in FIG. 3, an apparatus 150 uses a first and second configurable optics 152, 154 for source selection. Since apparatus 150 uses some of the same element configuration as apparatus 100, the same reference numerals are employed to designate corresponding parts.

Apparatus 150 uses a long-wavelength source 156 that is positioned at a first focal point of an ellipsoidal reflector 158. Ellipsoidal reflector 158 belongs to first configurable optics 152, that also include a removable plane mirror 160. Together, reflector 158 and mirror 160 shape long-wavelength radiation 106 such that it enters short-wavelength source 108 via passage 112. This is accomplished because pinhole 112 is located at the second focus of ellipsoidal reflector 158, which corresponds to the point to which long-wavelength radiation 106 is refocused.

Second configurable optics 152 consist of a spherical reflector 162 for shaping short-wavelength radiation 110 exiting through passage 112. Specifically, reflector 162 re-focuses radiation 110 such that it re-enters source 108 through passage 112 and exits through exit window 122.

Apparatus 150 can be operated in a number of modes. For example, first configurable optics 152 can be adjusted by moving plane mirror 160 belonging to it into position as shown by arrow A. In this configuration, when source 108 is turned on, both long- and short-wavelength radiation 106, 110 is combined in beam 130 and irradiates the sample at spot 134. In another mode, while keeping configurable optics 152 in the same position, source 108 can be turned off to examine the sample with long-wavelength radiation 106 only. In still another mode, mirror 160 is removed, as indicated by arrow B and now measurements can be performed with short-wavelength radiation 110 only.

In addition to the modalities in which apparatus 150 can be operated, it also has the advantage of using only reflective optical elements. This is particularly important for good stability and focusing of beam 130 and collection of signal beam 138 at sampling pinhole 140 when using the full bandwidth, i.e., both long- and short-wavelength radiation 106, 110.

Still another embodiment of the invention using configurable optics is exemplified in apparatus 170. Apparatus 170 is shown in a first configuration in FIG. 4A and in a second configuration in FIG. 4B. The same numerals are used to designate previously described elements for convenience.

In FIG. 4A apparatus 170 uses a first configurable optics 172 in the form of an ellipsoidal reflector. Reflector 172 is moved into position such its second focus is coincident with passage 112. As in the previous embodiment, long-wavelength source 156 is positioned at the first focus of reflector 172. In this configuration, beam 130 can contain either long- or short-wavelength radiation 106, 110, or both.

Figure 4B:
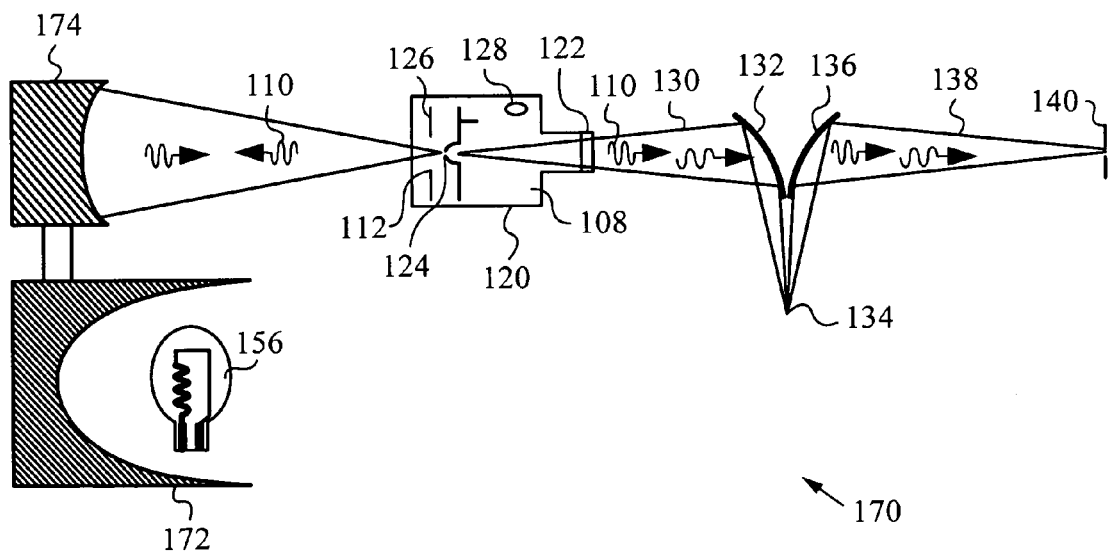

In FIG. 4B apparatus 170 uses a second configurable optics 174 in the form of a spherical reflector. Reflector 174 is moved into position such that it re-focuses short-wavelength radiation 110 leaving source 108 through passage 112, back into pinhole 112. In this configuration, beam 130 contains short-wavelength radiation 110.

FIG. 5 illustrates a portion of still another apparatus 200 in accordance with the invention. As in several of the previous embodiments, apparatus uses short-wavelength source 108 to produce short-wavelength radiation 110. Unlike the above embodiments, however, apparatus 200 uses two emitters to produce long-wavelength radiation 202 covering a wavelength range up to 3,000 nm. Apparatus 200 employs a visible wavelength emitter 204 for emitting visible radiation 202A and an infrared wavelength emitter 206 for emitting infrared radiation 202B. Both emitters 204, 206 use ellipsoidal reflectors 208, 210 in their optics to shape and direct radiation 202A, 202B, respectively.

A beam combining mechanism 212 in the form of a beam splitter/combiner is used to combine visible and infrared radiation 202A, 202B into a beam 214 of long-wavelength radiation 202. Coatings with suitable anti-reflective and reflective properties can be used to ensure efficient operation of beam combiner 212 over the entire wavelength range. Additional optics, including lenses and/or reflective optical elements (not shown) can be used to further ensure that radiation 202 is properly admitted into short-wavelength source 108 via passage 112 in anode 126. A person skilled in the art will be familiar with appropriate materials, elements and methods.

FIG. 6. illustrates a portion of an apparatus 220, which employs short-wavelength source 108 and emitters 204, 206 in a configurable embodiment. Specifically, apparatus 220 uses configurable optics 222A, 222B and 222C to enable the user to select the wavelengths of radiation used for metrology or scatterometry. Optics 222B, 222C are in the form of ellipsoidal reflectors and optics 222A are in the form of a spherical reflector.

A mobile stage 224 is used to move configurable optics 222A, 222B and 222C in and out of the optical path of apparatus 220. In the configuration shown, radiation 202A and 110 are contained in a signal beam 226 issuing forth through exit window 122.

In still another embodiment of the invention, or any of the above-described embodiments, it is advantageous to maintain long- and short-wavelength sources in a common housing. The housing should be kept close to room temperature by any suitable cooling system. For example, a closed-loop liquid cooling system can be used for this purpose. Alternatively, the cooling system is a forced-convection system using fins and fans. Preferably, both long- and short-wavelength sources are further equipped with a fitting such that they can be attached to the common housing.

The fitting on each source lamp allows it to fit into the common housing and be perfectly aligned, oriented, and spaced along a center optical axis of the beam. The precision machined housing cavities for each bulb determine the distance each bulb is apart by tightly fitting around the fitting diameter. Precision reference pins that interact with the fitting determine the angular orientation of the lamp. The distance from the fitting flange to the center of the bulb is precision aligned. When the bulb is placed in the housing, the flange mounting distance allows for accurate placement in the x-y plane.

In adjusting the apparatus of invention to any particular use, it is important to select sources that ensure appropriate intensity at different wavelengths. The graph in FIG. 9 shows the effect of different visible emitters (lamps) on the intensity of the light at different wavelengths. The highest intensity is obtained by halogen lamp at 27 W. The Xe lamp provides lower intensity than the halogen lamp but higher than the W lamp. At wavelengths less than 250 nm none of the three lamps offer any significant contribution to radiation intensity.

FIG. 10 is a graph of the reflectivity of reflectors that can be used for the reflective beam combining optics. They use a highly reflective (HR) silver-coated film that is significantly more reflective at shorter wavelengths than a conventional reflective (CR) film.

FIG. 11 illustrates the change in light intensity with wavelength at the detector as a conventional coated reflector is brought in and out of the beam path during time period NR. The sources are a halogen lamp and a deuterium lamp. The reflector increased the intensities down to 350 nm. In FIG. 12 the same situation is shown in the case of a tungsten and deuterium lamp. Once again, the reflector is absent during time period NR.

FIG. 13 shows the sampling size for optical analysis on the sample as measured by the knife-edge technique for conventional tungsten/deuterium broad band source with a 40 µm sampling pinhole labeled by A as compared to a halogen/deuterium broad band source with a 20 µm sampling pinhole labeled as B placed before the detector. Both provide comparable intensity at the detector. The apparatus of the invention provides higher lateral resolution and it therefore capable of probing a smaller spot on the sample.

Finally, FIG. 14 illustrates an application of a device in accordance with the invention using the small and intense spot to examine a three-dimensional structure etched in silicon. The arrangement is analogous to the one illustrated in FIG. 1. The angle of incidence of the broadband beam onto the sample with the three-dimensional structure etched in silicon is 4 degrees. The incident light is $R_s$ polarized. The etched structure consists of 9.5 µm deep circular pores etched into the silicon substrate. Of course, the three-dimensional structures that can be examined can also include deep trenches or any other surface features, especially ones that are deep and require IR wavelengths for examination. In the present example, the pores are 100 nm in diameter and lie on a square lattice with a lattice pitch of 500 nm. The signal beam that scatters from the sample bears a classic interference pattern that is dependent on pore depth and width.

Two features of the apparatus configuration in accordance with the invention help to enhance the results obtained. First, the wavelength of broadband beam extends beyond the silicon band gap, so that the silicon sample is transparent with respect to the incident light. Second, the wavelength of the light in the broadband beam is much larger than feature size, to that the structure in the spectrum has a uniform film-like quality and is not complicated by heavy diffraction effects.

The detector used for examining the IR portion of the signal beam can be of any of several different types of IR spectrometers that are commercially available. For example, InGaAs array spectrometers from Ocean Optics Inc. (www.oceanoptics.com) and B&W TEK Inc (www.bwtek.com) provide spectral range from 0.9~2.2 µm. PbS 256 elements photo diode arrays spectrometers from B&W TEK Inc and Spectral Products (www.spectralproducts.com/catalog/product_info.php?products_id=83/SM301_SM301-EX_Pb-S_PbSe_Spectrometer.php) cover 1.1~2.9 µm spectrum range and are also appropriate. Spectral Products also provides a PbSe array spectrometer which covers 1.5~5 µm that can be used in applications where the very large bandwidth capability of the apparatus of invention is extended considerably beyond 3,000 nm.

Clearly, the apparatus and method of invention can be employed in many situations. The wide spectral band and small spot size are key for many metrology applications and thus many other embodiments of the apparatus and method are possible. Therefore, the scope of the invention should be judged by the appended claims and their legal equivalents.

We claim:

1. An apparatus for examining features of a sample with a broadband beam, said apparatus comprising:
   a) a long-wavelength source for emitting a long-wavelength radiation;
   b) a short-wavelength source for emitting a short-wavelength radiation;
   c) a passage between said long-wavelength source and said short-wavelength source;
   d) a reflective beam combining optics for shaping said long-wavelength radiation to enter said short-wavelength source via said passage, and for shaping said short-wavelength radiation exiting through said passage to re-enter said short-wavelength source via said passage, thereby combining said long-wavelength radiation and said short-wavelength radiation into said broadband beam exiting said short-wavelength source;
   e) a beam steering optics for projecting said broadband beam to a spot on said sample;
   f) a beam intercepting optics for intercepting a scattered broadband radiation from said spot to produce a broadband signal beam;
   g) a sampling pinhole for passing a test portion of said broadband signal beam corresponding to a center portion of said spot; and
   h) a detector for examining said test portion.

2. The apparatus of claim 1, wherein said long-wavelength source comprises a visible wavelength emitter for emitting a visible radiation and an infrared wavelength emitter for emitting an infrared radiation.

3. The apparatus of claim 2, further comprising a beam combining mechanism for combining said visible radiation and said infrared radiation into a beam of said long-wavelength radiation.

4. The apparatus of claim 2, further comprising a mobile stage for moving said visible wavelength emitter and said infrared wavelength emitter from between said reflective beam combining optics and said passage.

5. The apparatus of claim 1, wherein said reflective beam combining optics comprise a concave reflector selected from the group consisting of a spherical mirror and an ellipsoidal mirror.

6. The apparatus of claim 5, wherein said concave reflector has a broadband reflective coating.

7. The apparatus of claim 5, further comprising a refractive element positioned between said long-wavelength source and said passage for further shaping said long-wavelength radiation and said short-wavelength radiation.

8. The apparatus of claim 7, further comprising a second mobile stage for inserting and removing said refractive element and said long-wavelength source from between said concave reflector and said passage.

9. The apparatus of claim 1, wherein said short-wavelength source comprises a wide-band casing consisting of a material selected from the group consisting of quartz, $MgF_2$ and synthetic silica.

10. The apparatus of claim 1, wherein said long-wavelength source comprises at least one emitter selected from the group consisting of halogen lamp, discharge lamp and an infrared lamp, and said short-wavelength source comprises a DUV deuterium lamp.

11. The apparatus of claim 10, wherein said long-wavelength source and said short-wavelength source are fitted in a common housing.

12. The apparatus of claim 11, wherein at least one of said long-wavelength source and said short-wavelength source comprises a fitting for attachment to said common housing.

13. The apparatus of claim 1, wherein said sample comprises a three-dimensional structure.

14. The apparatus of claim 13, wherein said three-dimensional structure is selected from the group consisting of pores and trenches.

15. An apparatus for examining features of a sample with a long-wavelength radiation and a short-wavelength radiation, said apparatus comprising:
a) a long-wavelength source for emitting said long-wavelength radiation;
b) a short-wavelength source for emitting said short-wavelength radiation;
c) a passage between said long-wavelength source and said short-wavelength source;
d) a first configurable optics for shaping said long-wavelength radiation to enter said short-wavelength source via said passage;
e) a second configurable optics for shaping said short-wavelength radiation exiting through said passage to re-enter said short-wavelength source via said passage and exit said short-wavelength source;
f) a beam steering optics for projecting said long-wavelength radiation and said short-wavelength radiation to a spot on said sample;
g) a beam intercepting optics for intercepting a scattered long-wavelength radiation and a scattered short-wavelength radiation from said spot to produce a broadband signal beam;
h) a sampling pinhole for passing a test portion of said broadband signal beam corresponding to a center portion of said spot; and
i) a detector for examining said test portion.

16. The apparatus of claim 15, wherein said long-wavelength source comprises a visible wavelength emitter for emitting a visible radiation and an infrared wavelength emitter for emitting an infrared radiation.

17. The apparatus of claim 16, wherein said first configurable optics comprise a beam combining mechanism for combining said visible radiation and said infrared radiation into a beam of said long-wavelength radiation.

18. The apparatus of claim 16, further comprising a mobile stage for moving said visible wavelength emitter and said infrared wavelength emitter from between said first configurable optics and said passage.

19. The apparatus of claim 15, wherein said first configurable optics comprise at least one element selected from the group consisting of, ellipsoidal mirror, spherical mirror and removable plane mirror.

20. The apparatus of claim 15, wherein said second configurable optics comprise a spherical mirror.

21. The apparatus of claim 15, wherein at least one of said first configurable optics and said second configurable optics are movable.

22. The apparatus of claim 21, wherein said first configurable optics and said second configurable optics are moved such that only one of said long-wavelength radiation and said short-wavelength radiation is projected to said spot on said sample at a time.

23. The apparatus of claim 15, wherein said sample comprises a three-dimensional structure.

24. The apparatus of claim 23, wherein said three-dimensional structure is selected from the group consisting of pores and trenches.

25. A method for examining features of a sample with a short-wavelength radiation and a long-wavelength radiation, said method comprising:
a) emitting a long-wavelength radiation from a long-wavelength source;
b) emitting a short-wavelength radiation from a short-wavelength source;
c) providing a passage between said long-wavelength source and said short-wavelength source;
d) shaping said long-wavelength radiation to enter said short-wavelength source via said passage and exit said short-wavelength source;
e) shaping said short-wavelength radiation exiting through said passage to re-enter said short-wavelength source via said passage and exit said short-wavelength source;
f) projecting said long-wavelength radiation to a spot on said sample;
g) projecting said short-wavelength radiation to a spot on said sample;
h) intercepting a scattered portion of at least one of said long-wavelength radiation and said short-wavelength radiation scattered at said spot; and
i) sampling a test portion of said scattered portion through a sampling pinhole.

26. The method of claim 25, wherein said long-wavelength radiation and said short-wavelength radiation are projected to said spot at the same time.

27. The method of claim 25, wherein said long-wavelength radiation and said short-wavelength radiation are projected to said spot at different times.

28. The method of claim 25, further comprising limiting the cross-section of said long-wavelength radiation and said short-wavelength radiation.

29. The method of claim 25, wherein said step of projecting comprises projecting said spot on a three-dimensional structure of said sample.

30. The method of claim 29, wherein said three-dimensional structure is selected from the group consisting of pores and trenches.

* * * * *